United States Patent [19]

Seelich

[11] Patent Number: 4,909,251

[45] Date of Patent: Mar. 20, 1990

[54] TISSUE ADHESIVE

[75] Inventor: Thomas Seelich, Vienna, Austria

[73] Assignee: Immuno Aktiengesellschaft fur chemisch-medizinische Produkte, Vienna, Austria

[21] Appl. No.: 359,346

[22] Filed: May 31, 1989

[30] Foreign Application Priority Data

May 31, 1988 [AT] Austria .................................. 1420/88

[51] Int. Cl.⁴ ....................... A61B 17/04; A61K 3/14; C08L 89/00
[52] U.S. Cl. ...................................... 606/213; 106/157; 106/124; 106/161; 424/101; 514/2; 514/802
[58] Field of Search ..................... 128/334 R; 106/157, 106/124, 161; 424/101, 177; 514/2, 802; 530/380, 384

[56] References Cited

U.S. PATENT DOCUMENTS

| | | | |
|---|---|---|---|
| 4,362,567 | 12/1982 | Schwarz et al. | 106/157 |
| 4,414,976 | 11/1983 | Schwarz et al. | 128/334 R |
| 4,427,650 | 1/1984 | Stroetmann | 424/46 |
| 4,427,651 | 1/1984 | Stroetmann | 424/46 |
| 4,442,655 | 4/1984 | Stroetmann | 106/124 |
| 4,627,879 | 12/1986 | Rose et al. | 106/124 |

FOREIGN PATENT DOCUMENTS

| | | | |
|---|---|---|---|
| 1168982 | 6/1984 | Canada | 128/334 R |
| 1182444 | 2/1985 | Canada | 128/334 R |

Primary Examiner—Edward M. Coven
Assistant Examiner—Gary Jackson
Attorney, Agent, or Firm—Burns, Doane, Swecker & Mathis

[57] ABSTRACT

A tissue adhesive in lyophilized form contains at least one biologically compatible tenside beside fibrinogen and factor XIII and optionally further proteins as well as adjuvants or additives. The presence of these biologically compatible tensides was found to shorten the reconstitution times of lyophilized tissue adhesive preparations without negatively affecting the biochemical, mechanical or biological properties of the preparation or of the fibrin formed therefrom.

20 Claims, No Drawings

TISSUE ADHESIVE

The invention relates to a tissue adhesive for seamlessly or seam-supportingly connecting human or animal tissue or organ parts, for sealing wounds, stopping bleeding, stimulating wound healing and the like, in lyophilized form and having a content of fibrinogen of at least 0.25 (25% by mass) and a content of factor XIII, the ratio of factor XIII to fibrinogen, expressed in units of factor XIII per gram of fibrinogen, being at least 150.

Tissue adhesives of this type have already been known from U.S. Pat. Nos. 4,362,567 and 4,414,976 and Can. Pat. No. 1,168,982. In addition to fibrinogen and factor XIII they contain further proteins, such as fibronectin and albumin, and optionally antibiotics.

Their mode of action is based on the fact that, due to the action of thrombin, the (soluble) fibrinogen present in the reconstituted tissue adhesive is converted into (insoluble) fibrin and factor XIII is activated to factor XIIIa. The latter cross-links the fibrin formed to give a high polymer, which is essential to the effectiveness of the tissue adhesive. The thrombin activity required may be derived either from the tissue to be glued itself (the wound areas), or it may be added to the tissue adhesive at gluing in the form of a solution containing thrombin and $Ca^{2+}$ ions.

Such preparations i.a. allow for a reliable stopping of bleeding, make for a good adhering capacity of the tissue adhesive to the wound or tissue surfaces, and provide for a high straining capacity of the glued sites or sealed wounds, and a complete absorbability of the tissue adhesive in the course of the wound healing process; and they have properties which stimulate wound healing.

Tissue adhesives are commercially available either in the form of deep-frozen solutions or as lyophilisate, because they are not very stable as liquid aqueous solutions and are not durable over longer periods of time. Therefore, the commerically available products must be either thawed prior to their application or they must be reconstituted from their lyophilisates. Both measures involve a considerable loss of time.

On the part of the physicians there is the wish for a shortening of the dissolution periods, since particularly in emergency situations involving surgery quick availability may be of decisive importance. This problem is particularly urgent when reconstituting a tissue adhesive lyophilisate, because for use as a tissue adhesive, fibrinogen concentrations of at least 70 mg/ml are necessary, which to obtain is often difficult and time consuming. This is, e.g., the case if the physiological salt content of the solution, i.e. the physiological ionic strength, must not be exceeded for reasons of biological compatibility (cf. Redl et al., Medizinische Welt, 1985,36, 769–76).

Particular difficulties arise from the requirement of an increased safety of the preparation with respect to the risk of transmitting pathogenic viruses (hepatitis, HIV) that may be contained in the starting material used (e.g. human blood plasma); for this reason it is necessary to subject the preparations to a virus-inactivating process, which preferably is carried out such that the pulverulent material is heated in closed containers for a predetermined period of time, while controlling its humidity content. However, this further adversely affects the solubility of the fibrinogen product. This is even more so when carrying out other virus inactivation methods, e.g. when heating the solution in the presence of stabilizing agents.

For the reasons stated there have been numerous attempts at improving the reconstitution time of lyophilized preparations. Can. Pat. No. 1,182,444 for instance, describes a method and an arrangement for accelerating the dissolution of lyophilized medicines. The combined heating and stirring device disclosed there did mean a progress, i.e. markedly shortened reconstitution times, yet physicians have voiced their desire for further improvements.

It has been known that the solubility of hard-soluble proteins can be improved by certain additions. Thus, EP-A-0 085 923 discloses a lyophilized fibrinogen composition which, besides fibrinogen, contains a further substance having a urea or guanidine residue. It has, however, been shown that such additions have a cytotoxic effect, inhibit the growth of fibroblasts and cause a changed, unphysiological fibrin structure resulting in the loss of the desired elasticity of the fibrin (cf. Redl et al., loc. cit.). With the inhibition of growth of fibroblasts, i.e. those cells that initiate the wound healing process, the desired properties of fibrinogen-based tissue adhesives of stimulating wound healing are lost. Due to the missing elasticity of the fibrin formed furthermore the high straining capacity of the gluings in vivo is jeopardized.

The present invention aims at providing a tissue adhesive which does not exhibit the disadvantages discussed, which, however, requires a substantially reduced reconstitution time as compared to the prior art.

According to the invention this object is achieved in that the tissue adhesive contains at least one biologically compatible tenside in addition to fibrinogen and optionally further proteins as well as adjuvants or additives. It has surprisingly been found that the presence of these biologically compatible tensides substantially reduces the reconstitution time without exhibiting the above-mentioned detrimental effects.

This is even more surprising, since tensides have generally been believed by those skilled in the art to have a denaturing effect on fibrinogen and have even been used as precipitating agents for fibrinogen (cf. Kurioka and Inove: "Interaction of Fibrinogen with Detergent", J. Biochem 77, 449–455, 1975).

In particular it could be shown that fibrinogen-based tissue adhesives containing tensides in concentrations that cause a substantial shortening of the reconstitution time of the lyophilized preparations are not cytotoxic, do not inhibit the growth of fibroblasts and do not change the typical spatially branched structure of a physiological fibrin clot as well as its mechanical properties (ultimate tensile strength and elasticity). This holds true for a great number of tensides of the most varying chemical structures of all four tenside classes, i.e. non-ionic, zwitterionic, anionic and cationic tensides.

The use according to the invention of tensides in tissue adhesive preparations is indicated in any case in which the prepartions are subjected to a virus inactivation method in the course of their production, i.e. it is meaningful even if the preparations finally are to be made storable not by lyophilizing, but by deep-freezing the solution ready for use. This is, e.g., the case if the product is lyophilized at an intermediary stage and is subjected to a heating procedure for the purpose of virus inactivation. The tenside admixed facilitates redissolving of the heated intermediate product and allows for rapid further processing.

Thus, the addition of the tenside may be effected at various stages of the production process; in particular, prior as well as subsequent to the carrying out of a virus inactivation method. It may be suitable for the tissue adhesive to further contain an antioxidant for stabilization purposes.

Advantageously, the tissue adhesive contains at least one tenside from the groups of the non-ionic, cationic, anionic or zwitterionic tensides in an amount of from 0.0003 to 0.15 (0.03 to 15% by mass), preferably 0.001 to 0.01 (0.1 to 1% by mass) based on the fibrinogen content.

According to a preferred embodiment, the tissue adhesive according to the invention is reconstitutable with aqua ad iniectabilia to give a solution ready for use having a concentration of at least 70 mg of fibrinogen/ml, which solution has an osmolarity of 0.70 osmol at the most, and its electroylte content is limited such that after a further ten-fold dilution with aqua ad iniectabilia the electric conductivity at 20° C. is 3 mS at the most.

It is known that a tissue adhesive whose solution ready for use has an unphysiologically high ionic strength and/or osmolarity is cytotoxic.

The addition of tensides enables a shortening of the reconstitution time of the lyophilized tissue adhesive according to the invention without increasing the ionic strength and/or osmolarity of the solution ready for use such that any damage to the cells can be observed.

As the measure of the allowable electrolyte content of a preparation according to the invention suitably the electric conductivity of the solution ready for use obtainable therefrom may be used, since an exact measurement of the latter can be performed in a simple manner.

A particular characteristic of the reconstituted tissue adhesive according to the invention is, after its application, a complete cross-linking capacity of the fibrin-gamma-chains after 3 to 5 minutes and a cross-linking capacity of the fibrin-alpha-chains of at least 60% after two hours, after mixing with a solution containing thrombin and $Ca^{2+}$ ions and incubation at 37° C., determined by means of the sodium lauryl sulfate (SDS) polyacryl amide gel electrophoresis.

It has proved to be favorable for the tissue adhesive to contain a tenside selected from the groups of the polyether-alcohols comprising polyoxyethylene(23)-dodecyl ether, polyoxyethylene(10)-hexadecyl ether, polyoxyethylene(20)-hexadecyl ether, octylphenolpolyethyleneglycol(30)-ether, octylphenolpolyethyleneglycol(12–13)-ether, octylphenolpolyethyleneglycol(7–8)-ether, octylphenolpolyethylene glycol(40)-ether, and octylphenolpolyethyleneglycol-ether-formaldehyde polymers, of the polyether-esters, such as polyethylenglycol-660-12-hydroxystearate, polyoxy-ethylenestrearoylester, or of the polyoxy-ethylene-polyoxypropylene block polymers.

The reconstitution time can also be shortened if the tissue adhesive contains a tenside of the group of the sugar esters, such as sucrose-palmitate-stearate, of the polyalcohol-anhydride-esters, such as sorbitan-monolaurate or sorbitan-monooleate, of the glycosides, such as octyl-$\beta$-D-glucopyranoside, of the alkinoles, such as 2,4,7,9-tetramethyl-5-decin--4,7-diol, of the aminoxides, such as dodecyl-dimethyl-aminoxide, or of the hydroxyalkylamides.

The same positive effect can be observed in a tissue adhesive containing a tenside from the group of the sulfosuccinates, such as dioctylsulfosuccinate, or of the alkaline salts of the bile acids, such as Na-desoxycholate. The compounds mentioned belong to the class of the anionic tensides.

Furthermore, it is advantageous for the tissue adhesive to contain a tenside from the group of the substituted ammonium salts, such as benzyl-dimethyl-2-hydroxy-ethyl-ammonium-chloride or benzyl trimethyl ammonium chloride, or of the alkyl-pyridinium salts, such as cetyl-pyridinium-chloride. These tensides are cationic by nature.

The presence of zwitterions also shortens the reconstitution time. Advantageously, a tissue adhesive according to the invention may contain a tenside from the group of the phosphatides, such as lecithin, or a tenside from the group of the sulfobentaines, such as N-dodecyl-N'N-dimethyl-ammonio-3-propane-sulfonate, of the zwitterionic bile acid derivatives, such as 3-(3-cholamidopropyl)-dimethylamino-1-propane sulfonate, of the alkyl betaines, of the sarcosines, such as N-lauroyl sarcosine, or of the imino-dipropanoic acids, such as N-lauryl-$\beta$-imino-dipropanoic acid.

If desired, the preparation according to the invention will contain an additional antioxidant to stabilize it, in particular if a virus inactivation method is carried out.

As a further advantageous embodiment, the tissue adhesive according to the invention may additionally contain substances having an antimicrobial activity.

The invention also comprises the use of a lyophilized composition on the basis of human or animal proteins having a content of fibrinogen of at least 0.25 (25% by mass) of the dry substance, a content of factor XIII in an amount of at least 150 units per gram of fibrinogen, and a content of at least one biologically compatible tenside, the total tenside content being of from 0.0003 to 0.15 (0.03 to 15% by mass) of the fibrinogen content, optionally having a content of fibronectin of up to 0.65 (65% by mass) of the fibrinogen content, and optionally having a content of albumin of up to 1.1 of the fibrinogen content, for the production of a tissue adhesive solution ready for use in a concentration of at least 70 mg of fibrinogen/ml for seamlessly or seam-supportingly connecting human or animal tissue or organ parts, for sealing wounds, stopping bleeding, stimulating wound healing.

The invention will be explained in more detail below.

(A) Examples 1 to 37

280 l of fresh human plasma, frozen at $-20°$ C. were heated to $+2°$ C., the cryoprecipitate formed was separated by centrifugation, treated with a buffer solution of pH 6.5 containing 6.6 g of $Na_3$ citrate.$2H_2O$, 3.4 g of NaCl, 10.0 g of glycine, 25,000 KIU of aprotinine and 200 I.U. of heparin per liter, and was again centifuged at $+2°$ C. The separated precipitate was divided into portions of about 50 g and was stored at $-20°$ C. until further processing. Individual portions were then thawed and dissolved in further buffer solutions of pH 7.9, containing 19.0 g of human albumin, 9.0 g of glycin, 1.0 g of trisodium citrate.$2H_2O$, 25,000 KIU of aprotinin and 2000 I.U of heparin per liter, which furthermore contained various tensides in varying concentrations, and were adjusted to a protein concentration of 50 g/l.

The determination of the protein content was effected according to Kjeldahl.

For producing a comparative solution (control), a portion of the separated precipitate was dissolved and diluted with the same buffer solution as described above, yet without the addition of a tenside.

Then the diluted tissue adhesive solutions were sterile-filtered and filled in portions of 2.5 ml each into final containers (glass bottles), a part of these final containers being provided with a magnetic or magnetizable stirring body. Thereafter they were deep-frozen in the usual manner, lyophilized, the final containers were sealed so as to be air-tight and stored at +4° C. until they were used for the tests described below.

For generally characterizing the preparations, the following determinations were carried out:
dry substance per final container,
total protein (according to Kjeldahl)
relative content of fibrinogen, fibronectin and albumin by SDS polyacryl amide gel electrophoresis in the presence of urea (M. Furlan et al.: Plasmic degradation of human fibrinogen. IV. Identification of subunit chain remnants in fragment Y. Biochim. Biophys, Acta 400, 112-120 (1975), in particular page 114), i.e. (a) of a nonreduced sample, and (b) of a sample reduced with $\beta$-mercaptoethanol, staining with Coomassie Blue and densitometric evaluation (T. Seelich, H. Redl: Theoretische Grundlagen des Fibrinklebers, K. Schimpf: Fibrinogen, Fibrin und Fibrinkleber, F. K. Schattauer Verlag, Stuttgart-N.Y., 1980, pages 199-208).

In sample (a), albumin is obtained as an isolated protein band from which the albumin content (in % of the total protein) results directly. Sample (b) shows the following isolated bands: fibronectin, fibrinogen-Aalpha, Bbeta and gamma chains, wherein it must be noted that in the fibrinogen-Bbeta band also albumin is contained. From sample (b) there results directly the content of fibronectin; the fibrinogen content results from the sum of the fibrinogen Aalpha, Bbeta, and gamma bands after subtraction of the albumin value obtained from sample (a).

From the thus obtained values of fibrinogen, fibronectin and albumin (in % of the total protein) and the separately determined total protein it is possible to calculate the content of these three proteins per ml or per final container.

The fibrinogen content was additionally determined according to the rules of USP XVI, page 298, as the protein clottable by thrombin according to the method of Kjeldahl, the two methods yielding values well in agreement.

For determining the fibrinogen content of the dry substance, the value obtained according to the USP method was used.

The content of factor XIII was determined in the following manner by means of a fibrin cross-linking test, in which fibrinogen free of factor XIII is used as the substrate:

0.5 ml each of a fibrinogen solution free of factor XIII having a fibrinogen content of 10 mg/ml are mixed with 0.05 ml each of various dilutions of the sample to be determined and 0.1 ml each of a solution containing 60 I.U. of thrombin and 130 myMol of $CaCl_2$ per ml and incubated at 37° C. After an incubation period of 2 hours, the reaction is stopped by adding a mixture of urea, Na-dodecyl sulfate (SDS) and beta-mercaptoethanol, and the disulphide bridges contained in the proteins are cleaved by reduction. The degree of cross-linking of the fibrin gamma chains is densitometrically determined after SDS polyacryl amide gel electrophoresis (M. Furlan et al.: Plasmic degradation of human fibrinogen. IV. Identification of subunit chain remnants in fragment Y. Biochim. Biophys. Acta 400, 112-120 (1975), in particular page 114) of the thus obtained samples and staining with Coomassie Blue and serves as a measure for the factor XIII content.

As the standard, pooled human citrated plasma is used, 1 ml of plasma containing 1 unit of factor XIII per definitionem. Those dilutions of the sample and the standard, which cause a 50% cross-linking of the fibrin gamma chains under the test conditions, are determined, and the factor XIII content (X) of the original sample is calculated according to the formula $$X = \frac{Vx}{Vs}$$

wherein Vx is the dilution of the unknown sample and Vs is the dilution of the standard.

From the content of factor XIII thus determined and the fibrinogen content determined as above, the ratio of units of factor XIII to grams of fibrinogen was calculated.

Electric conductivity:
Determination after ten-fold dilution of the tissue adhesive solution ready for use with distilled water by using a CDM-3-conductometer of Radiometer Copenhagen at 20° C.

Osmolarity:
Determination with a vapour pressure osmometer of Wescor, U.S.A.

The effectiveness and harmlessness of the tensides added were tested in the following manner:
Reconstitution time:

That time was measured in minutes, which was necessary to completely dissolve the lyophilisate after the addition of 1.0 ml of solvent ($H_2O$ or aqueous aprotinin solution, 3000 KIU/ml) at 37° C. The mixing of lyophilisate and solvent necessary for dissolving was effected according to two methods: Bottles without a magnetic stirring body were slightly shaken by hand (Method I), and in bottles equipped with a stirring body, a combined stirring and heating apparatus was used. This was a special magnetic stirring device operable by induction and heatable (Fibrinotherm$^R$, Immuno AG, Vienna).

The reconstitution times given in Table 1 are arithmetic mean values of three determinations each.

Content of clottable protein (fibrinogen): see above.
Cross-linking capacity of the fibrin alpha chains:
Determination of the cross-linking capacity of the fibrin alpha chains was effected according to a cross-linking test (T. Seelich, H. Redl: "Theoretische Grundlagen des Fibrinklebers" in K. Schimpf: "Fibrinogen, Fibrin und Fibrinkleber", F. K. Schattauer Verlag, Stuttgart-N.Y., 199-208, 1980) in which, after mixing of the dissolved tissue adhesive ready for use with an equal volume of a solution containing 40 myMol of $CaCl_2$ and 15 I.U. of thrombin per ml, the mixture is incubated at 37° C. The degree of cross-linking of the fibrin alpha chains is densitometrically determined after stopping the reaction and reductively cleaving the disulphide bridges contained in the proteins by the addition of a mixture of urea, Na-dodecylsulfate (SDS) and beta-mercaptoethanol by means of SDS polyacrylamide gel electrophoresis and staining with Coomassie Blue.

Characterization of the fibrin formed:

As has already been descsribed in various publications, the kind of the fibrin structure formed can be recognized already macroscopically: the typical, spatially branched structure which forms under physiological conditions expresses itself macroscopically in the form of white, tough-elastic clots ("coarse clots"). Under unphysiological conditions, however, transparent brittle, so-called "fine clots" form (cf. Ferry and Morrison, J, Am. Chem. Soc 69, 388–400, 1947; Redl et al., Med. Welt 36, 769–776, 1985).

Thus, to characterize the fibrin formed, equal volumes of the tissue adhesive solution ready for use to be tested and of a thrombin-$CaCl_2$ solution (15 I.U. of thrombin and 40 myMol of $CaCl_2$ per ml) were mixed at 37° C., and after about 10 min the appearance and the consistency (strength, elasticity) of the fibrin clot formed were judged.

Cytocompatibility
according to Redl et al., Medizinische Welt36, 769–776, 1985:

The tissue adhesive solution to be tested was diluted with isotonic saline solution 1+1, and this solution was superposed on living human fibroblasts of the lung that had been grown in cell culture until a a uniform cell sheet had formed. A possible damaging effect of the tissue adhesive (or of the tenside contained therein, respectively) on the living cells was observed in the light-optical microscope. After an incubation period of approximately 1 hour the cells were fixed and stained for a more precise assessment.

In separate tests increasing amounts of NaCl or sucrose were added to the tissue adhesive solutions constituting the comparative formulations to Examples 1–37, and with these solutions the above-described test for cytocompatibility were carried out. These tests were intended for finding that electrolyte content and that osmolarity from which a cytotoxic effect could be observed.

It was found that a cytotoxic effect occurred from an osmolarlity of more than 0.70 osm and/or from an electric conductivity (of the solution diluted ten times with aqua ad iniectabilia according to the above-described test) of more than 3 mS.

As regards their compositions, Examples 1 to 37 as well as the pertaining comparative example differ only in their different or missing tenside contents. The fibrinogen content was from 48 to 51% of the dry substance, these slight differences being caused by the different tenside contents.

After reconstitution of the lyophilisate contained in a final container with 1.0 ml of $H_2O$, a fibrinogen concentration of approximately 80 mg/ml was obtained. The relative content of fibrinogen was determined to be 64%, that of fibronectin to be 4.7% and that of albumin to be 26% of the total protein. Hence results a mass ratio of fibronectin to fibrinogen of 0.07 and of albumin to fibrinogen of 0.41.

In all the Examples the electric conductivity (after a further ten-fold dilution with $H_2O$) was about 1.3 mS at 20° C., i.e. the relatively low tenside addition had no apparent influence on the electric conductivity.

Likewise, all the Examples showed an osmolarity (of the concentrated tissue adhesive solutions) of approximately 0.45 osmol. The ratio of units of factor XIII to gram of fibrinogen was 170 in all the Examples.

The unexpected favorable influence of tensides on the reconstitution time of lyophilized tissue adhesive preparations can be seen in Table 1, which also indicates the content of clottable protein and the cross-linking capacity of the fibrin-alpha chains.

Numbers 1 to 37 denote Examples of tissue adhesive preparations containing different tensides whose precise chemical nature can be taken from Table 2. They prove that a plurality of non-ionic, zwitterionic, anionic and cationic tensides are suitable to substantially shorten the reconstitution time. By the tenside addition the lyophilisate could be dissolved, both according to Method I and to Method II, about twice to three times as fast as the comparative sample for Examples 1 to 37, whose reconstitution time was 15 minutes according to Method I and 7 min when using the combined stirring and heating device (Method II).

The tensides added had practically no influence on the clottability of the fibrinogen and only a slight influence on the cross-linking capacity of the fibrin-alpha chains.

The advantageous biochemical, physical and biological properties of the preparations were not negatively affected by the tenside addition. In all cases they proved to be non-cytotoxic, and the fibrin clots forming were white and had the desired tough-elastic consistency.

Examples 17, 21 and 37 show that also combinations of various tensides can be used to shorten the reconstitution time without undesired side-effects.

Example 37 shows in particular that even combinatons of anionic and cationic tensides yield the desired results. The two tensides A2 and K1 were used at an equimolar ratio, whereby, similar to zwitterionic tensides, the added tensides all together have the same number of positive and negative charges.

Examples 31 to 36 shows that also anionic or cationic tensides alone can be used successfully. Example 23 shows the use of a non-ionic tenside (N17) from the group of the polyether alcohols which additionally contains an antioxidant for stabilizing purposes (protection from auto-oxidation).

The following Examples 38 to 42 show that an equally favorable effect is achieved if the fibrinogen preparation is subjected to a virus inactivation procedure.

Examples 38 and 38a

A tissue adhesive preparation was prepared in a manner similiar to Examples 1 to 37, yet 10 units of factor XIII per ml were added to the diluted solution. Thereupon the solution was deep-frozedn as a whole, lyophilized and heated from 30 h at 60° C. under $N_2$ atmosphere at a water content of 0.005 (0.5% by mass).

Subsequently, the heated lyophilisate was divided into two parts and dissolved with $H_2O$ (comparison) on the one hand and with an 0.01% by weight aqueous solution of the tenside Pluronic F108 (cf. Table 2) on the other hand, to give a protein concentration of 50 g/l. Both solutions were sterile-filtered and filled in portions of 2.5 ml each into final containers (glass bottles) with or without stirring body, deep-frozen and lyophilized.

After reconstitution with 1.0 ml of $H_2O$ (Example 38) or aqueous aprotinin solution (Example 38a), respectively, tissue adhesive solutions ready for use having about 80 mg of fibrinogen/ml were obtained. The reconstitution times required were 7 min for the tenside-containing preparation of the invention according to Method I (shaking by hand) and 3 to 4 min according to Method II (using the combined heating and stirring device).

For the comparative preparation that did not contain a tenside, the corresponding times were 20 and 9 min, respectively. The ratio of factor XIII to fibrinogen was determined to be approximately 420 units per gram.

Apart therefrom, the two preparations did not differ noticeably from each other and their other properties corresponded to those of the tissue adhesive preparatoins described in Examples 1 to 37.

Example 39

Diluted tissue adhesive solutions without a tenside content (part I) and having a content of Triton WR 1339 (cf. Table 2) at a concentration of 0.1 g/l (part II) were prepared as described in Examples 1 to 37, yet 15,000 units of factor XIII per 1 were additionally added to the solutions.

Both solutions were then lyophilized as a whole, adjusted to a water content of 0.075 (7.5% by weight) and heated at 60° C. for 10 h under $N_2$ atmosphere. Thereupon both parts were dissolved to a protein concentration of 50 g/l. The dissolution of part I took longer and was incomplete; on the contrary, part II was easily and completely soluble. Both parts were filtered to be clear at first and subsequently were sterile-filtered, filled in portions of 5 ml each into final containers (glass bottles) with or without a magnetic stirring body and deep-frozen and lyophilized in the usual manner.

After reconstitution with 2.0 ml of $H_2O$, tissue adhesive solutions ready for use having approximately 80 mg of fibrinogen/ml were obtained. The reconstitution times required were 8 min according to Method I (shaking by hand) and 4 min according to Method II (combined heating and stirring device) for the tenside-containing preparation of the invention.

For the comparative preparation that did not contain a tenside the corresponding times were 25 and 12 min, respectively.

The ratio of factor XIII to fibrinogen was approximately 520 U/g; the other properties of the two preparations corresponded to those of the preceding Examples.

Example 40 (Heat-treated tissue adhesive having a tenside and antibiotic content)

The tenside-free or tenside-containing heat treated lyophilized tissue adhesive preparations were produced as in the preceding Example 39, yet 20 units of factor XIII per ml were added to the diluted tissue adhesive solutions and the lyophilisates were dissolved with an aqueous solution containing 18 g of gentamycin per 1 that had been adjusted to pH 7.3 with NaOH.

The solutions were sterile filtered, filled in portions of 12.5 ml each into final containers containing a stirring body and lyophilized.

After reconstitution with 5.0 ml of $H_2O$ or an aqueous aprotinin solution tissue adhesive solutions having about 80 mg of fibrinogen/ml and a gentamycin content of 45 mg/ml were obtained.

The fibrinogen content of the lyophilized preparation was 38% by mass, the ratio of factor XIII to fibrinogen was approximately 750 units per gram. The electric conductivity (after ten-fold dilution with $H_2O$) was 2.2 mS, the osmolarity of the concentrated solution ready for use was 0.61 osm.

The reconstitution time required (Method II) was 4 min for the tenside-containing preparation according to the invention, but 25 min for the tenside-free, yet antibiotic-containing comparative preparation.

Hence results that in that case the tenside content of the preparation is of particular advantage, since the solubility of the lyophilized tissue adhesive preparation deteriorates due to the antibiotic content per se as illustrated by a comparison with a tenside and antibiotic-free comparative preparation (Comparison to 39). This undesired effect of the antibiotic is completely compensated by the tenside content.

Example 41 (Removal of lipophil components by adding a non-ionic tenside, heating to beyond the turbidity point and subsequent phase separation)

A diluted tissue adhesive solution was produced as in the comparison to Examples 1 1 to 37. 15 units of factor XIII per ml were added to the solution, the solution was maintained at approximately 15° C., and 5% by volume of a solution containing 10 g of Pluronic L 61 (cf. Table 2) per liter were added under stirring. Thereupon the solution was slowly heated to about 30° C. under stirring. The resulting emulsion was separated into two phases by strong centrifugation (approximately 30,000 $\times$ g, 30 min, 30° C.).

The lower-lying phase poor in tenside (=main amount) was further processed after that treatment. Thereby lipophil hard soluble components were removed from the diluted tissue adhesive solution.

It was found that under the conditions stated the residual tenside content of the phase poor in tenside is about 0.02 g/l.

The purified diluted tissue adhesive solution thus obtained was lyophilized as a whole, adjusted to a water content of 0.075 (7.5% by mass) and heated at 60° C. for 10 h under $N_2$ atmosphere. Thereupon the lyophilisate was dissolved to a protein concentration of 50 g/l, filtered to be clear at first and subsequently sterile-filtered and filled in portions of 12.5 ml each into final containers (glass bottles) with or without a magnetic stirring body and deep-frozen and lyophilized in the usual manner.

After reconstitution with 5.0 ml of solvent ($H_2O$ or an aqueous aprotinin solution), tissue adhesive solutions ready for use having a fibrinogen content of approximately 80 mg/ml were obtained.

The reconstitution times required were 13 min according to Method I and 7 min according to Method II (comparison: 25 and 12 minutes, respectively).

The ratio of factor XIII to fibrinogen was 510 U/g. The other properties of the preparations corresponded to those of Examples 1 to 39.

Example 42

The procedure of Example 41 was repeated, yet after dissolving of the heat treated lyophilisate, 0.1 g of Triton WR-1339 (cf. Table 2) per liter were additionally added to the diluted tissue adhesive solution. A comparison with Example 41 (Table 1) shows that even better results could be achieved in this manner.

The following Example 43 shows that purification of the diluted tissue adhesive solution (removal of lipophil components) is possible also with a tenside that is practically insoluble in $H_2O$ and that is added as an emulsion. The subsequent additoin of a water-soluble tenside also yields very good results.

Example 43

Procedure as in Example 42, yet instead of a solution of Pluronic L 61 (cf. Table 2), 5% by volume of a 1% by weight-suspension of Span 80 (cf. Table 2) in H₂O were added to the diluted tissue adhesive solution, and the mixture was stirred for 30 min at room temperature. The tenside Span 80 (cf. Table 2) is nearly insoluble in H₂O.

After separation of the phases by centrifuging at 20° C., 0.1 g of Triton WR-1339 (cf. Table 2) per liter were further added to the diluted tissue adhesive solution. It was further proceeded as in Examples 41 and 42. The reconstitution times required were 5.5 min according to Method I and 3 min according to Method II (comparison: 13 and 7 minutes, respectively).

The following Examples 44 to 47 show a favorable influence of tensides on the reconstitution times of lyophilized tissue adhesive preparations, even if these preparations are produced according to other methods than those hitherto described and their protein compositions, in particular in respect of the ratios of fibronectin to fibrinogen and of albumin to fibrinogen, are modified.

Albumin had been contained in all hitherto known lyophilized tissue adhesive preparations based on fibrinogen and factor XIII, because it improves the solubility of such preparations substantially. the addition of a slight amount of a biologically compatible tenside according to the invention makes it possible to produce such preparations without an albumin content, these preparations nevertheless being very easily reconstitutable, as illustrated by the following Example 44:

Example 44

To 10 l of pooled human citrated plasma 1500 g of powderized glycine were added under stirring at room temperature, the pH was adjusted to 7.35, and the mixture was stirred for a further hour at room temperature. The precipitate formed was separated by centrifuging and dissolved with 1.5 l of a solution containing 9.0 g of NaCl and 2.9 g of Na₃-citrate.2H₂O per liter.

Precipitation with glycine was repeated in an analogous manner as described above by adding 225 g of glycine. After separation of the precipitate by centrifuging, the latter was mixed with half the amount of H₂O and dyalized against a solution containing 3.6 g of NaCl and 1.2 g of Na₃-citrate.2 H₂O per liter, ph, 7.35, at 4° C., subsequently liquefied by heating to 37° C. and adjusted with the same solution to a protein concentration of 40 g/l.

For producing a comparative preparation without a tenside content, a part of the solution was sterile-filtered and filled in portions of 2.5 ml each into final containers, deep-frozen and lyophilized analogously to the preceding Examples.

To the other part of the solution, the tenside WR 1339 (cf. Table 2) was added in a concentration of 0.1 mg/ml, and the solution was also sterile-filtered, filled in containers and lyophilized.

The preparations thus obtained had a fibrinogen content of 85% by weight and were practically free from albumin and fibronectin. The ratio of factor XIII to fibrinogen was 175 units/g.

After reconstitution with 1.0 ml of solvent (H₂O or aprotinin solution) tissue adhesive solutions ready for use having a fibrinogen content of about 95 mg/ml were obtained.

The electric conductivity (after a further 10-fold dilution with H₂O) was 1.8 mS; the osmolarity of the concentrated solution ready for use was 0.35 osm.

The reconstitution times required (Method II) amounted to about 35 min for the comparative preparation without tenside, but only 3.5 min for the tenside-containing preparation according to the invention.

The Example shows that especially with such lyophilized preparations that are particularly difficult to dissolve as such the inventive addition of a biologically compatible tenside leads to an enormuous and unexpected improvement in the solubility. Thus it becomes possible for the first time to dispense with the relatively expensive human albumin which is available only to a limited extent, as a solubilizer.

Example 45

20 g of a human plasma cryoprecipitate, obtained according to Examples 1 to 43, were dissolved with 2.0 l of a solution containing 9.0 g of NaCl, 2.9 g of Na₃-citrate.2H₂O and 25,000 KIU of aprotinin per liter, and heated to 37° C. Thereupon 165 g powderized glycine were added slowly under stirring, and the solution was stirred for a further hour under cooling to 20° C. The precipitate formed was separated by centrifuging, washed at 0° to 2° C., with a 16-fold amount of a buffer solution containing 1.2 g of NaCl, 25,000 KIU of aprotinin and 2.4 g of Na₃-citrate.2 H₂O per liter, pH 7.35, and again separated by centrifuging at 0° to 2° C. Then the precipitate was dissolved with the above-mentioned buffer solution which additionally contained 9.0 g of glycine per liter, and adjusted to a protein concentration of 30 mg/ml.

Subsequently, 5% by volume of a 20% by weight human albumin solution, 15 mg of purified lyophilized fibronectin and 5 units of factor XIII per ml were added to this solution.

For making a comparative preparation without a tenside content, a part of the solution was sterile-filtered and filled in portions of 2.6 ml each into final containers, deep-frozen and lyophilized analogous to the preceding Examples.

To the other part of the solution, the tenside Triton WR 1339 (cf. Table 2) was added at a concentration of 0.15 mg/ml and the solution was also sterile-filtered, filled into containers and lyophilized.

The preparation thus obtained had the following composition:
fibrinogen: 41% by mass of the dry substance,
ratio factor XIII to fibrinogen: 340 U/g,
mass ratio fibronectin to fibrinogen: 0.58,
mass ratio albumin to fibrinogen: 0.35.

After reconstitution with 1.0 ml of solvent (H₂O or aprotinin solution) a tissue adhesive solution ready for use having a fibrinogen content of 72 mg/ml was obtained.

The reconstitution times required (Method II) were 15 min for the comparative preparation without tenside, but only 4 min for the tenside-containing preparation according to the invention.

The electric conductivity (after a 10-fold dilution with H₂O) was 1.3 mS, the osmolarity of the concentrated solution ready for use was 0.45 osm.

The Example shows the favorable influence of the tenside content on the reconstitution times of lyophilized tissue adhesive preparations having a high content of fibronectin, which, similar to fibrinogen, belongs to those plama proteins which are difficult to dissolve. The fibronectin content increases the adhesive capability of the adhesive on the tissue and its properties of stimulating wound healing.

Example 46

The preparation of a diluted tissue adhesive solution having a fibrinogen content of 30 mg/ml was repeated according to Example 45.

Subsequently, 13% by volume of a 20% by weight human albumin solution, 3 mg of purified lyophilized fibronectin and 5 units of factor XIII per ml were added. For making a comparative preparation without a tenside content, a part of the solution was steril-filtered and filled in portions of 14.0 ml each into final containers, deep-frozen and lyophilized analogous to the preceding Examples.

To the other part of the solution the tenside WR 1339 (cf. Table 2) was added at a concentration of 0.1 mg/ml and the solution was also sterile filtered, filled into containers and lyophilized.

The preparations thus obtained had the following composition:
fibrinogen: 40% by mass of the dry substance,
ratio factor XIII to fibrinogen: 350 U/g,
mass ratio fibronectin to fibrinogen: 0.13,
mass ratio albumin to fibrinogen: 0.90.

After reconstitution with 5.0 ml of solvent, a tissue adhesive solution ready for use having a fibrinogen content of about 72 mg/ml was obtained.

The reconstitution times required (Method II) were 12 min for the comparative preparation without tenside, yet only 4 min for the tenside-containing preparation according to the invention.

The Example shows the favorable effect of the tenside content on the reconstitution times of lyophilized tissue adhesive preparations having a particularly high total protein content (149 mg/ml) and a particularly high mass ratio of albumin to fibrinogen.

The albumin content has a stabilizing effect on the preparation, particularly if the latter is subjected to a virus inactivation method (e.g. by heating).

Example 47

4.0 l of human pooled citrated plasma were mixed with 100,000 KIU of aprotinin, and thereupon 760 ml of an ammonium sulphate solution saturated at room temperature were added, the pH was adjusted to 7.0, and the mixture was stirred over night at 4° C.

The precipitate formed was separated by centrifuging and dissolved with 1.0 l of a buffer solution having a pH of 7.4, containing 18.0 g of NaCl, 14.7 g $Na_3$-citrate.2 $H_2O$ and 25,000 KIU of aprotinin per liter.

A slight amount of insoluble material was removed by centifuging, and the precipitation was repeated with ammonium sulphate in an analogous manner.

The precipitate formed was separated by centrifuging, dialyzed at 4° against a buffer solution having a pH of 7.35, containing 3.6 g of NaCl and 1.2 g $Na_3$-citrate.2-$H_2O$ per liter, subsequently liquefied by heating to 37° C., adjusted with the same buffer solution to a protein concentration of 40 mg/ml, and 3% by volume of a 20% by weight human albumin solution and 4 units of factor XIII per ml were added. For making a comparative preparation without a tenside content, a part of the solution was sterile-filtered and filled in portions of 5.0 ml each into final containers, deep-frozen and lyophilized analogous to the preceding Examples.

To the other part of the solution, the tenside Solutol HS 15 (cf. Table 2) was added at a concentration of 0.12 g/l, and the solution was further processed in the same manner.

After reconstitution with 2.0 ml of solvent ($H_2O$ or aprotinin) tissue adhesive solutions ready for use having a fibrinogen content of 84 mg/ml were obtained.

The reconstitution times required (Method II) were approximately 25 min for the comparative preparation without tenside, yet only 5 min for the tenside-containing preparation according to the invention.

Besides, the preparations had the following composition and properties:
fibrinogen: 71% by mass of the dry substance,
ratio factor XIII to fibrinogen: 265 U/g,
mass ratio fibronectin to fibrinogen: 0.095,
mass ratio albumin to fibrinogen: 0.18.

Electric conductivity (after a 10-fold dilution with $H_2O$): 2.0 mS; osmolarity of the concentrated solution ready for use: 0.36 osm.

The Example shows that also with this altered production method and at a relatively low albumin content (wherein preparations are obtained which as such are relatively difficult to dissolve) the inventive addition of a biologically compatible tenside leads to a substantial improvement in the solubility.

All the preparations according to the invention, described in Examples 1 to 47 proved to be non-cytotoxic and formed white fibrin clots of the desired tough-elastic consistency.

The most essential properties of these preparations (as well as the pertaining comparative preparations) are listed in Table 1.

TABLE 1

| Example | Tenside | Ratio tenside: fibrinogen (g/g) | S | Method I DT in min | Method II DT in min | Clottable Protein (g/l) | alpha-p (%) | Remarks |
| --- | --- | --- | --- | --- | --- | --- | --- | --- |
| Comparison for 1-37 | — | — | $H_2O$ | 15 | 7 | 81 | 85 | |
| Comparison for 1-37 | — | — | aprotinin* | 15 | 8 | 81 | 86 | |
| 1 | N1 | 0.0038 | $H_2O$ | 5 | 2.5 | 79 | 79 | |
| 2 | N1 | 0.0038 | aprotinin | 6 | 3 | 80 | 81 | |
| 3 | N1 | 0.0012 | $H_2O$ | 8 | 4 | 81 | 81 | |
| 4 | N2 | 0.0125 | $H_2O$ | 6 | 3.5 | 80 | 77 | |
| 5 | N2 | 0.0038 | $H_2O$ | 7 | 4 | 80 | 83 | |
| 6 | N2 | 0.0013 | $H_2O$ | 8 | 4.5 | 80 | 82 | |
| 7 | N3 | 0.0063 | aprotinin | 8,5 | 4 | 79 | 75 | |
| 8 | N4 | 0.0123 | $H_2O$ | 7 | 3.5 | 81 | 80 | |
| 9 | N5 | 0.013 | $H_2O$ | 5 | 2.5 | 80 | 82 | |

TABLE 1-continued

| Example | Tenside | Ratio tenside: fibrinogen (g/g) | S | Method I DT in min | Method II DT in min | Clottable Protein (g/l) | alpha-p (%) | Remarks |
|---|---|---|---|---|---|---|---|---|
| 10 | N6 | 0.013 | H$_2$O | 7 | 3 | 79 | 80 | |
| 11 | N7 | 0.128 | H$_2$O | 5 | 2 | 78 | 65 | |
| 12 | N7 | 0.038 | H$_2$O | 5 | 2 | 79 | 75 | |
| 13 | N7 | 0.012 | H$_2$O | 5 | 2 | 81 | 80 | |
| 14 | N7 | 0.0038 | H$_2$O | 6 | 3 | 80 | 79 | |
| 15 | N7 | 0.0038 | aprotinin | 6 | 3 | 80 | 80 | |
| 16 | N7 | 0.0012 | H$_2$O | 13 | 6 | 81 | 83 | |
| 17 | N5<br>N7 | 0.0019<br>0.0019 | aprotinin | 6 | 3 | 80 | 78 | |
| 18 | N8 | 0.0013 | H$_2$O | 12 | 6 | 79 | 80 | |
| 19 | N11 | 0.0013 | H$_2$O | 10 | 5 | 80 | 82 | |
| 20 | N12 | 0.013 | H$_2$O | 10 | 4.5 | 80 | 81 | |
| 21 | N7<br>N9 | 0.013<br>0.0004 | H$_2$O | 4.5 | 2 | 80 | 82 | |
| 22 | N13 | 0.0038 | H$_2$O | 8 | 3.5 | 79 | 83 | |
| 23 | N17 | 0.0013 | H$_2$O | 8 | 4 | 81 | 83 | N17 contains an antioxidant |
| 24 | Z1 | 0.013 | H$_2$O | 7 | 3.5 | 80 | 77 | |
| 25 | Z1 | 0.013 | aprotinin | 7 | 3.5 | 81 | 79 | |
| 26 | Z2 | 0.004 | H$_2$O | 10 | 5 | 81 | 80 | |
| 27 | Z3 | 0.004 | H$_2$O | 9 | 4 | 81 | 77 | |
| 28 | Z4 | 0.004 | H$_2$O | 10 | 4.5 | 80 | 79 | |
| 29 | Z5 | 0.004 | H$_2$O | 8 | 4 | 79 | 82 | |
| 30 | Z6 | 0.013 | H$_2$O | 6 | 3 | 81 | 80 | |
| 31 | A1 | 0.013 | H$_2$O | 8 | 3.5 | 80 | 78 | |
| 32 | A1 | 0.013 | aprotinin | 7.5 | 3.5 | 80 | 80 | |
| 33 | A2 | 0.004 | H$_2$O | 10 | 5 | 79 | 81 | |
| 34 | K1 | 0.004 | H$_2$O | 8 | 3.5 | 80 | 77 | |
| 35 | K1 | 0.004 | aprotinin | 7.5 | 3.5 | 80 | 82 | |
| 36 | K2 | 0.004 | H$_2$O | 8 | 4 | 80 | 79 | |
| 37 | A2<br>K1 | 0.013<br>0.006 | H$_2$O | 7.5 | 3.5 | 81 | 80 | |
| Comparison for 38 | — | — | H$_2$O | 20 | 10 | 80 | 95 | |
| Comparison for 38a | — | — | aprotinin | 20 | 9 | 81 | 93 | |
| 38 | N5 | 0.003 | H$_2$O | 7 | 3 | 81 | 91 | |
| 38a | N5 | 0.003 | aprotinin | 7 | 4 | 80 | 92 | |
| Comparison for 39 | — | — | aprotinin | 25 | 12 | 78 | 89 | |
| 39 | N7 | 0.003 | aprotinin | 8 | 4 | 80 | 91 | |
| Comparison for 40 | — | — | aprotinin | — | 25 | 81 | 85 | with antibiotic |
| 40 | N7 | 0.003 | aprotinin | — | 4 | 80 | 86 | with antibiotic |
| Comparison for 41, 42, 43 | — | — | — | 25 | 12 | 78 | 89 | |
| 41 | N19 | 0.0006 | aprotinin | 13 | 7 | 79 | 90 | |
| 42 | N19<br>N7 | 0.0006<br>0.003 | aprotinin | 5 | 2.5 | 79 | 93 | |
| 43 | N20<br>N7 | n.d.<br>0.003 | H$_2$O | 5.5 | 3 | 80 | 92 | |
| Comparison for 44 | — | — | aprotinin | — | 35 | 94 | 87 | |
| 44 | N7 | 0.0026 | aprotinin | — | 3.5 | 95 | 85 | |
| Comparison for 45 | — | — | H$_2$O | — | 15 | 72 | 92 | |
| 45 | N7 | 0.0054 | H$_2$O | — | 4 | 72 | 90 | |
| Comparison for 46 | — | — | H$_2$O | — | 12 | 72 | 95 | |
| 46 | N7 | 0.0039 | H$_2$O | — | 4 | 73 | 95 | |
| Comparison for 47 | — | — | aprotinin | — | 25 | 84 | 88 | |
| 47 | N1 | 0.0036 | aprotinin | — | 5 | 84 | 87 | |

TABLE 1-continued

| Example | Tenside | Ratio tenside: fibrinogen (g/g) | S | Method I DT in min | Method II DT in min | Clottable Protein (g/l) | alpha-p (%) | Remarks |
|---|---|---|---|---|---|---|---|---|
| | | tinin | | | | | | |

*Aprotinin = aqueous aprotinin solution having 3000 KIU/ml
S = solvent
DT = dissolution time (reconstitution time)
alpha-p = cross-linking of fibrin-alpha chains (Fb-alpha-polymer)
n.d. = not determined

TABLE 2

| Code of the tenside | chemical name | Trade name |
|---|---|---|
| N1 | Polyethylene-glycol-660-12-hydroxystearate | Solutol HS 15 |
| N2 | Polyoxyethylene-(approx. 40)-stearoyl-ester | Myrj 52 |
| N3 | 2,4,7,9-tetramethyl-5-decin-4,7-diol | Surfynol |
| N4 | Polyethylene-glycol(20)-sorbitan-monooleate | Tween 80 |
| N5 | Polyoxyethylene-polyoxypropylene-block polymer | Pluronic F 108 |
| N6 | Octyl-β-D-glycopyranoside | — |
| N7 | Formaldehyde-polymer of octylphenol-polyoxyethylene-ether | Triton WR 1339 |
| N8 | Dodecyldimethylaminoxide | — |
| N9 | Sorbitan-monolaurate | Span 20 |
| N10 | Octylphenol-polyethylene-glycol(40)ether | Triton X-405 |
| N11 | Sucrose-palmitate-stearate (SPS 15) | — |
| N12 | N-D-Gluco-N-methyldecanamide (Mega 10) | — |
| N13 | Octylphenol-polyethylene-glycol(7–8)ether | Triton X-114 |
| N14 | Octylphenol-polyethylene-glycol(12–13)ether | Triton X-102 |
| N15 | Octylphenol-polyethylene-glycol(30)ether | Triton X-305 |
| N16 | Polyoxyethylene(10)hexadecyl-ether | Brij 56 |
| N17 | Polyoxyethylene(20)hexadecyl-ether | Brij 58 |
| N18 | Polyoxyethylene(23)dodecyl-ether | Brij 35 |
| N19 | Polyoxyethylene-polyoxypropylene-block polymer | Pluronic L 61 |
| N20 | Sorbitan-monooleoate | Span 80 |
| A1 | Dioctylsulfosuccinate | — |
| A2 | Na-Desoxycholate | — |
| C1 | Benzyldimethyl-2-hydroxyethyl-ammoniumchloride | — |
| C2 | Benzyltrimethylammoniumchloride | — |
| C3 | Cetylpyridiniumchloride | — |
| Z1 | 3-(3-Cholamidopropyl)-dimethylammonio-1-propane-sulphonate (Chaps) | — |
| Z2 | Lecithin | — |
| Z3 | N-Dodecyl-N',N-dimethylammonio-3-propane-sulphonate (Sulfobetain SB 12) | — |
| Z4 | N-Laurylβ-iminodipropanoic acid | — |
| Z5 | Alkyl-betain | Empigen BB |
| Z6 | N-Lauroyl-sarcosine | Sarkosyl NL-35 |

N: non-ionic
A: anionic
C: cationic
Z: zwitterionic

What I claim is:

1. In a tissue adhesive for seamlessly or seam-supportingly connecting human or animal tissue or organ parts, for sealing wounds, stopping bleeding and stimulating wound healing in lyophilized form and having a fibrinogen content of at least 0.25 (25% by mass) and a factor XIII content, the ratio of factor XIII to fibrinogen, expressed in units of factor XIII per gram of fibrinogen being at least 150, the improvement comprising at least one biologically compatible tenside in addition to fibrinogen.

2. A tissue adhesive as set forth in claim 1, wherein at least one tenside from the group of the non-ionic, cationic, anionic and zwitterionic tensides is present in an amount of from 0.003 to 0.15 (0.03 to 15% by mass) based on the fibrinogen content.

3. A tissue adhesive as set forth in claim 2, wherein said tenside is present in an amount of from 0.001 to 0.01 (0.1 to 1.0% by mass).

4. A tissue adhesive as set forth in claim 2, wherein said tissue adhesive contains a tenside selected from the groups of the polyether-alcohols, comprising polyoxyethylene(23)-dodecyl-ether,
polyoxyethylene(10)-hexadecyl-ether,
polyoxyethylene(20)-hexadecyl-ether,
octylphenolpolyethylenglycol(30)-ether,
octylphenolpolyethyleneglycol(12-13)-ether,
octylphenolpolyethyleneglycol(7-8)-ether,
octylphenolpolyethyleneglycol(40)-ether, and
octylphenolpolyethyleneglycol-ether-formaldehydepolymers,
the polyether esters, or
the polyoxyethylene-polyoxypropylene-block polymers.

5. A tissue adhesive as set forth in claim 4 wherein the tenside is a polyethylene glycol-660-12-hydroxystearate or a polyoxyethylene-stearoyl ester.

6. A tissue adhesive as set forth in claim 2, wherein said tissue adhesive contains a tenside from the group of the sugar esters, the polyalcohol-anhydride esters, the glycosides, the alkinols, the amine-oxides, or the hydroxyalkyl-amides.

7. A tissue adhesive as set forth in claim 6 wherein the tenside is sucrose palmitate stearate, sorbitan monolaurate, sorbitan monooleate, octyl-β-D-glucopyranoside, 2,4,7,9-tetramethyl-5-decin-4,7-diol, or docecyl-dimethyl-amineoxide.

8. A tissue adhesive as set forth in claim 2, wherein said tissue adhesive contains a tenside from the group of the sulfosuccinates, or the alkaline salts of the bile acids.

9. A tissue adhesive as set forth in claim 8 wherein the tenside is dioctyl-sulfosuccinate or Na-desoxycholate.

10. A tissue adhesive as set forth in claim 2, wherein said tissue adhesive comprises a tenside from the group of the substituted ammonium salts or of the alkyl-pyridinium salts.

11. A tissue adhesive as set forth in claim 10 wherein the tenside is benzyldimethyl-2-hydroxyethyl-ammonium chloride, benzy-trimethyl-ammonium chloride, or cetylpyridinium chloride.

12. A tissue adhesive as set forth in claim 2, wherein said tissue adhesive contains a tenside from the group of the phosphatides, or at least one tenside from the group of the sulfobetains, the zwitterionic bile acid derivatives, the alkylbetains, the sarcosines, or of the imino-dipropanoic acids.

13. A tissue adhesive as set forth in claim 10 wherein the tenside is lecithin, N-dodecyl-N',N-dimethylam-monio-3-propane sulfonate, 3-(3-cholamidopropyl)-dimethylamino-1-propane sulfonate, N-lauroylsarco-sine, or N-lauryl-β-imino-dipropanoic acid.

14. A tissue adhesive as set forth in claim 1, wherein said tissue adhesive is reconstitutable with aqua ad iniectabilia to give a solution ready for use having a concentration of at least 70 mg of fibrinogen/ml, said solution having an osmolarity of 0.70 osmol at the most, said tissue adhesive having an electrolyte content limited such that after a further ten-fold dilution with aqua ad iniectabilia the tissue adhesive has an electric conductivity at 20° C. of 3 mS at the most.

15. A tissue adhesive in reconstituted form as set forth in claim 14, wherein the fibrin-gamma chains are completely cross-linkable after 3 to 5 minutes and the fibrinalpha chains are cross-linkable to at least 60% after two hours, after mixing with a solution containing thrombin and $Ca^{2+}$ ions and incubation at 37° C., determined by sodiumlaurylsulphate-(SDS)-polyacrylamide gel electrophoresis.

16. A tissue adhesive as set forth in claim 1, further comprising an antoixdant.

17. A tissue adhesive as set forth in claim 1, further comprising additional substances having antimicrobial activities.

18. A method for seamlessly or seamsupportingly connecting human or animal tissue or organ part, for sealing wounds, stopping bleeding and stimulating wound healing comprising the application of a lyophilized composition based on human or animal proteins comprising a fibrinogen content of at least 0.25 (25% by mass) of the dry substance, a factor XIII content in an amount of at least 150 units per gram of fibrinogen, and a content of at least one biologically compatible tenside, the total tenside content being from 0.0003 to 0.15 (0.03 to 15% by mass) of the fibrinogen content, for producing a tissue adhesive solution ready for use at a concentration of at least 70 mg of fibrinogen/ml.

19. The method of claim 18 wherein the composition further comprises a fibronectin content of up to 0.65 (65% by mass) of the fibrinogen content.

20. The method of claim 18 wherein the composition further comprises an albumin content of up to 1.1 (110% by mass) of the fibrinogen content.

* * * * *